United States Patent [19]
Daeuble et al.

[11] Patent Number: 6,117,884
[45] Date of Patent: Sep. 12, 2000

[54] 4-SUBSTITUTED QUINOLINE DERIVATIVES HAVING FUNGICIDAL ACTIVITY

[76] Inventors: John Daeuble, 2783 Wooded Glen Ct., Indianapolis, Ind. 46268; L. Navell Davis, 10076 N. 700E, Morristown, Ind. 46161; Karin Hellwig, 4778 Stansbury La., Indianapolis, Ind. 46254; Neil Kirby, 13911 Stonemill Cir., Carmel, Ind. 46032; Marshall H. Parker, 771 Arrowwood Dr., Carmel, Ind. 46033; Mary Pieczko, 5323 Holly Springs W., Indianapolis, Ind. 46254; Lori K. Thomason, 1756 Shorter Dr., Indianapolis, Ind. 46214

[21] Appl. No.: 08/904,282

[22] Filed: Jul. 31, 1997

[51] Int. Cl.⁷ .................... C07D 215/18; C07D 215/12; A01N 43/42
[52] U.S. Cl. .................... 514/311; 546/152; 546/176; 546/179
[58] Field of Search ............... 514/311; 546/152, 546/176, 179

[56] References Cited

U.S. PATENT DOCUMENTS

| | | | |
|---|---|---|---|
| 4,680,291 | 7/1987 | Hamberger et al. | 514/183 |
| 4,939,148 | 7/1990 | Stutz et al. | 514/649 |
| 5,114,939 | 5/1992 | Dreikorn et al. | 514/248 |
| 5,145,843 | 9/1992 | Arnold et al. | 514/63 |
| 5,240,916 | 8/1993 | Caley et al. | |
| 5,240,940 | 8/1993 | Arnold et al. | 514/312 |
| 5,296,484 | 3/1994 | Coghlan et al. | 514/311 |

FOREIGN PATENT DOCUMENTS

| | | | |
|---|---|---|---|
| 0497371A1 | 8/1992 | European Pat. Off. | C07D 401/12 |
| 05301805 | 11/1993 | Japan | A01N 43/54 |
| 05301806 | 11/1993 | Japan | A01N 43/54 |
| 06049064 | 2/1994 | Japan | C07D 401/12 |

OTHER PUBLICATIONS

M. J. Coghlan et al, "Novel Agents for the Control of Cereal and Grape Powdery Mildew", Chapt 43, pp. 538–552, in *Synthesis and Chemistry of Agrochemicals II*, American Chemical Society (D. R. Baker et al.,editor, 1991).

*Primary Examiner*—Jose' G. Dees
*Assistant Examiner*—Sabiha N. Qozi
*Attorney, Agent, or Firm*—Carl D. Corvin; Donald R. Stuart

[57] ABSTRACT

This invention provides compounds of formula (1)

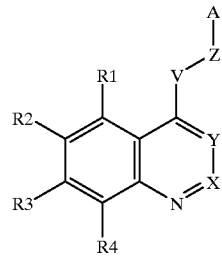

wherein the substituents are described in the specification. The compounds of formula (1) are plant fungicides.

13 Claims, No Drawings

4-SUBSTITUTED QUINOLINE DERIVATIVES HAVING FUNGICIDAL ACTIVITY

BACKGROUND OF THE INVENTION

This invention provides novel compounds which are 4-substituted quinoline derivatives having plant fungicidal activity. This invention also provides compositions and combination products containing one or more compounds of this invention as the active ingredient. Some of the combination products exhibit synergistic activity against plant pathogens. This invention also provides fungicidal methods.

SUMMARY OF THE INVENTION

This invention provides novel compounds of formula (1)

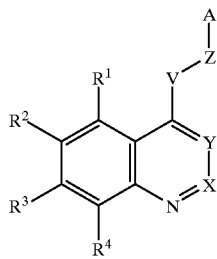

(1)

wherein
X is $CR^5$, where $R^5$ is H, Cl or $CH_3$;
Y is $CR^{5'}$ where $R^{5'}$ is H, Cl, or Br;
Z is O, S, SO, $SO_2$, $NR^6$, where $R^6$ is H, $C_1$–$C_4$ alkyl, $C_1$–$C_4$ acyl, $CR^7R^8$, where $R^7$ and $R^8$ are independently H, $C_1$–$C_4$ alkyl, $C_1$–$C_4$ alkenyl, $C_2$–$C_4$ alkynyl, $C_1$–$C_4$ acyl, CN, or OH, or $R^7$ and $R^8$ together combine to form a carbocyclic ring containing four to six carbon atoms;
$R^1$–$R^4$ are independently H, OH, $NO_2$, halo, I, $C_1$–$C_4$ alkyl, $C_3$–$C_4$ branched alkyl, $C_1$–$C_4$ alkoxy, halo $C_1$–$C_4$ alkyl, halo $C_1$–$C_4$ alkoxy, or halo $C_1$–$C_4$ alkylthio, or $R^1$ and $R^2$ or $R^2$ and $R^3$ together combine to form a carbocyclic ring containing four to six carbon atoms;
V is $CR^7R^8$ where $R^7$ and $R^8$ are independently H, $C_1$–$C_4$ alkyl, $C_1$–$C_4$ alkenyl, $C_2$–$C_4$ alkynyl, $C_1$–$C_4$ acyl, CN, optionally substituted phenoxy, halo $C_1$–$C_4$ alkyl, or OH, or $R^7$ and $R^8$ together combine to form a carbocyclic ring containing four to six carbon atoms;
A is
(a) a $C_1$–$C_{18}$ saturated or unsaturated straight or branched hydrocarbon chain, optionally including a hetero atom selected from O, S, SO, or $SO_2$, and optionally substituted with halo, halo $C_1$–$C_4$ alkoxy, OH, or $C_1$–$C_4$ acyl;
(b) $C_3$–$C_8$ cycloalkyl or cycloalkenyl;
(c) a phenyl group of formula (2)

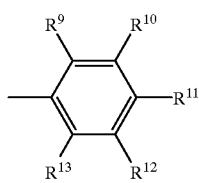

(2)

wherein
$R^9$–$R^{13}$ are independently H, CN, $NO_2$, OH, halo, $C_1$–$C_4$ alkyl, $C_3$–$C_4$ branched alkyl, $C_2$–$C_4$ alkanoyl, halo $C_1$–$C_7$ alkyl, hydroxy $C_1$–$C_7$ alkyl, $C_1$–$C_7$ alkoxy, halo $C_1$–$C_7$ alkoxy, $C_1$–$C_7$ alkylthio, halo $C_1$–$C_7$ alkylthio, phenyl, substituted phenyl, phenoxy, substituted phenoxy, phenylthio, substituted phenylthio, phenyl $C_1$–$C_4$ alkyl, substituted phenyl $C_1$–$C_4$ alkyl, benzoyl, $SiR^{20}R^{21}R^{22}$ or $OSiR^{20}R^{21}R^{22}$, where $R^{20}$, $R^{21}$, and $R^{22}$ are H, a $C_1$–$C_6$ straight chain or branched alkyl group, phenyl, or substituted phenyl, provided that at least one of $R^{20}$, $R^{21}$, and $R^{22}$ is other than H, or $R^{11}$ and $R^{12}$ or $R^{12}$ and $R^{13}$ combine to form a carbocyclic ring, provided that unless all of $R^9$–$R^{13}$ are H or F, then at least two of $R^9$–$R^{13}$ are H;
(d) a furyl group of formula (3)

(3)

wherein
$R^{14}$ is H, halo, halomethyl, CN, $NO_2$, $C_1$–$C_4$ alkyl, $C_3$–$C_4$ branched alkyl, phenyl, or $C_1$–$C_4$ alkoxy;
(e) a thienyl group of formula (4)

(4)

wherein
$R^{15}$ is H, halo, halomethyl, CN, $NO_2$, $C_1$–$C_4$ alkyl, $C_3$–$C_4$ branched alkyl, phenyl, or $C_1$–$C_4$ alkoxy;
(f) a group of formula (5) or (5a)

(5)

(5a)

wherein
$R^{16}$ is H, halo, halomethyl, CN, $NO_2$, $C_1$–$C_4$ alkyl, $C_3$–$C_4$ branched alkyl, phenyl, substituted phenyl, or $C_1$–$C_4$ alkoxy, and J is N or CH and G is O, $NR^{19}$ or CH, provided that either J is N or G is $NR^{19}$, where $R^{19}$ is H, $C_1$–$C_4$ alkyl, $C_1$–$C_4$ acyl, phenylsulfonyl, or substituted phenylsulfonyl;
(g) a group selected from pyridyl or substituted pyridyl;
(h) a group selected from pyrimidinyl or substituted pyrimidinyl; or
(i) a group selected from 1-naphthyl, substituted 1-naphthyl, 4-pyrazolyl, 3-methyl-4-pyrazolyl, 1,3-benzodioxolyl, tricyclo[3.3.1.1(3,7)]dec-2-yl, 1-(3-chlorophenyl)-1H-tetrazol-5-yl, pyridyl, substituted pyridyl, or an acid addition salt of a compound of formula (1), or an N-oxide of a compound of formula (1) where Y is CH.

DETAILED DESCRIPTION OF THE INVENTION

Throughout this document, all temperatures are given in degrees Celsius and all percentages are weight percentages, unless otherwise stated.

The term halo, used alone or in combination with other terms, refers to F, Cl, or Br.

The term "alkyl" refers to a straight chain alkyl radical.

The term "branched alkyl" refers to all alkyl isomers containing the designated number of carbon atoms, except the straight chain isomers.

The term "alkoxy" refers to a straight or branched chain alkoxy group.

The term "halo alkyl" refers to a straight or branched alkyl group, substituted with one or more halo atoms.

The term "halo alkoxy" refers to an alkoxy group, substituted with one or more halo atoms.

The term "halo alkylthio" refers to a straight or branched alkylthio group, substituted with one or more halo atoms.

The term "acyl" refers to straight or branched chain alkanoyl.

The term "substituted phenyl" refers to phenyl substituted with up to three groups selected from halo, $C_1$–$C_{10}$ alkyl, branched $C_3$–$C_6$ alkyl, halo $C_1$–$C_7$ alkyl, hydroxy $C_1$–$C_7$ alkyl, $C_1$–$C_7$ alkoxy, halo $C_1$–$C_7$ alkoxy, phenoxy, phenyl, $NO_2$, OH, CN, $C_1$–$C_4$ alkanoyloxy, or benzyloxy.

The term "substituted phenoxy" refers to a phenoxy group substituted with up to three groups selected from halo, $C_1$–$C_{10}$ alkyl, branched $C_3$–$C_6$ alkyl, halo $C_1$–$C_7$ alkyl, hydroxy $C_1$–$C_7$ alkyl, $C_1$–$C_7$ alkoxy, halo $C_1$–$C_7$ alkoxy, phenoxy, phenyl, $NO_2$, OH, CN, $C_1$–$C_4$ alkanoyloxy, or benzyloxy.

The term "substituted phenylthio" refers to a phenylthio group substituted with up to three groups selected from halo, $C_1$–$C_{10}$ alkyl, branched $C_3$–$C_6$ alkyl, halo $C_1$–$C_7$ alkyl, hydroxy $C_1$–$C_7$ alkyl, $C_1$–$C_7$ alkoxy, halo $C_1$–$C_7$ alkoxy, phenoxy, phenyl, $NO_2$, OH, CN, $C_1$–$C_4$ alkanoyloxy, or benzyloxy.

The term "substituted phenylsulfonyl" refers to a phenylsulfonyl group substituted with up to three groups selected from halo, I, $C_1$–$C_{10}$ alkyl, $C_3$–$C_6$ branched alkyl, halo $C_1$–$C_7$ alkyl, hydroxy $C_1$–$C_7$ alkyl, $C_1$–$C_7$ alkoxy, halo-$C_1$–$C_7$ alkoxy, phenoxy, phenyl, $NO_2$, OH, CN, $C_1$–$C_4$ alkanoyloxy, or benzyloxy.

The term "unsaturated hydrocarbon chain" refers to a hydrocarbon chain containing one to three multiple bond sites.

The term "carbocyclic ring" refers to a saturated or unsaturated ring of four to seven carbon atoms.

While all the compounds of this invention have fungicidal activity, certain classes of compounds may be preferred for reasons such as greater efficacy or ease of synthesis. These preferred classes include those compounds of formula (1), above, wherein X is $CR^5$ wherein $R^5$ is H;

Y is $CR^5$ wherein $R^5$ is H;

Z is O $R^1$–$R^4$ are independently H, halo, or $C_1$–$C_4$ alkyl, or more preferably halo;

V is CH or $C_1$–$C_4$ alkyl, and

A is a phenyl group of formula (2), above, wherein $R^9R^{13}$ are independently halo, $C_1$–$C_4$ alkyl, or halo C1–C7 alkyl, or more preferably a phenyl group of formula (2) above, wherein $R^9R^{13}$ is independently halo; a pyridyl or substituted pyridyl group; or a pyrimidinyl or substituted pyrimidinyl group.

The compounds of formula (1) have been found to control fungi, particularly plant pathogens. When employed in the treatment or prevention of plant fungal diseases, the compounds are applied to seeds or plants in a disease-inhibiting and phytologically-acceptable amount. The term "disease-inhibiting and phytologically-acceptable amount", as used herein, refers to an amount of a compound of the invention which kills or inhibits the plant disease for which control is desired, but is not significantly toxic to the plant. This amount will generally be from about 1 to 1000 ppm, with 10 to 500 ppm being preferred. The exact concentration of compound required varies with the fungal disease to be controlled, the type of formulation employed, the method of application, the particular plant species, climate conditions, and the like. The compounds of this invention may also be used to protect stored grain and other non-plant loci from fungal infestation.

The following tests were performed to determine the fungicidal efficacy of the compounds of this invention.

Fungicide Utility

The compounds of the present invention have been found to control fungi, particularly plant pathogens. When employed in the treatment of plant fungal diseases, the compounds are applied to the plants in a disease inhibiting and phytologically acceptable amount. As used herein, the term "disease inhibiting and phytologically acceptable amount", refers to an amount of a compound of the present invention which kills or inhibits the plant disease for which control is desired, but is not significantly toxic to the plant. This amount will generally be from about 1 to 1000 ppm, with 10 to 500 ppm being preferred. The exact concentration of compound required varies with the fungal disease to be controlled, the type formulation employed, the method of application, the particular plant species, climate conditions and the like. A suitable application rate is typically in the range from about 0.10 to about 4 lb/A. The compounds of the invention may also be used to protect stored grain and other non-plant loci from fungal infestation.

The following experiments were performed in the laboratory to determine the fungicidal efficacy of the compounds of the invention.

The test compounds were formulated for application by foliar spray. The following plant pathogens and their corresponding plants were employed.

| Pathogen | Designation in following Table | Host |
| --- | --- | --- |
| *Erysiphe graminis tritici* (powdery mildew) | PMW | wheat |

Screening Mehtof for PMW

Wheat c.v. Monon was grown in the greenhouse from seed in a soil-less peat-based potting mixture ("Metromix"). The seedlings were used for testing at the 1.5 leaf stage. Compound formulation was accomplished by dissolving technical materials in acetone, with serial dilutions then made in acetone to obtain desired rates. Final treatment volumes were obtained by adding nine volumes 0.011% aqueous Triton X-100, resulting in test solutions with 10% acetone and 0.01% Triton X-100. Test rates were 400, 100, 25, and 6.25 ppm.

In a high volume foliar application, plants were sprayed to runoff (using two opposing Spraying Systems 1/4JAUPM air atomization nozzles operated at approximately 138 kPa. Test inoculum for wheat powdery mildew (*E. graminis f.* sp. *tritici*) was produced in vivo on stock plants in the greenhouse. The test plants were inoculated by dusting spores from stock plants on test plants 24 hours after spray application After inoculation the test plants were kept in the greenhouse for seven days, until disease on the untreated control plants was fully developed. Seven days after inoculation, the disease incidence on the leaves was assessed visually.

The following table presents the activity of typical compounds of the present invention when evaluated in these experiments. The effectiveness of test compounds in controlling disease was rated using the following scale.

| COMPOUND NUMBER | RATE (ppm) | PMW |
|---|---|---|
| 1 | 400 | + |
| 1 | 100 | + |
| 1 | 25 | + |
| 1 | 6.25 | + |
| 2 | 400 | + |
| 2 | 100 | − |
| 2 | 25 | − |
| 2 | 6.25 | − |
| 3 | 400 | + |
| 3 | 100 | + |
| 3 | 25 | + |
| 3 | 6.25 | + |
| 4 | 400 | + |
| 4 | 100 | + |
| 4 | 25 | + |
| 4 | 6.25 | + |
| 5 | 400 | − |
| 5 | 100 | − |
| 5 | 25 | − |
| 5 | 6.25 | − |
| 6 | 400 | − |
| 6 | 100 | − |
| 6 | 25 | − |
| 6 | 6.25 | − |
| 7 | 400 | + |
| 7 | 100 | + |
| 7 | 25 | − |
| 7 | 6.25 | − |
| 8 | 400 | − |
| 8 | 100 | − |
| 8 | 25 | − |
| 8 | 6.25 | − |
| 9 | 400 | + |
| 9 | 100 | + |
| 9 | 25 | + |
| 9 | 6.25 | − |
| 10 | 400 | + |
| 10 | 100 | + |
| 10 | 25 | + |
| 10 | 6.25 | − |
| 11 | 400 | − |
| 11 | 100 | − |
| 11 | 25 | − |
| 11 | 6.25 | − |
| 12 | 400 | + |
| 12 | 100 | + |
| 12 | 25 | + |
| 12 | 6.25 | + |
| 13 | 400 | + |
| 13 | 100 | + |
| 13 | 25 | − |
| 13 | 6.25 | − |
| 14 | 400 | − |
| 14 | 100 | − |
| 14 | 25 | − |
| 14 | 6.25 | − |
| 15 | 400 | + |
| 15 | 100 | + |
| 15 | 25 | − |
| 15 | 6.25 | − |
| 16 | 400 | + |
| 16 | 100 | + |
| 16 | 25 | + |
| 16 | 6.25 | − |
| 17 | 400 | + |
| 17 | 100 | + |
| 17 | 25 | + |
| 17 | 6.25 | + |
| 18 | 400 | + |
| 18 | 100 | + |
| 18 | 25 | + |
| 18 | 6.25 | + |
| 19 | 400 | + |
| 19 | 100 | + |
| 19 | 25 | + |
| 19 | 6.25 | − |
| 20 | 400 | + |
| 20 | 100 | + |
| 20 | 25 | + |
| 20 | 6.25 | + |
| 21 | 400 | + |
| 21 | 100 | + |
| 21 | 25 | + |
| 21 | 6.25 | + |
| 22 | 400 | + |
| 22 | 100 | + |
| 22 | 25 | − |
| 22 | 6.25 | − |
| 23 | 400 | + |
| 23 | 100 | + |
| 23 | 25 | − |
| 23 | 6.25 | − |
| 24 | 400 | + |
| 24 | 100 | + |
| 24 | 25 | + |
| 24 | 6.25 | − |
| 25 | 400 | − |
| 25 | 100 | − |
| 25 | 25 | − |
| 25 | 6.25 | − |
| 26 | 400 | + |
| 26 | 100 | + |
| 26 | 25 | − |
| 26 | 6.25 | − |
| 27 | 400 | + |
| 27 | 100 | + |
| 27 | 25 | + |
| 27 | 6.25 | − |
| 28 | 400 | + |
| 28 | 100 | − |
| 28 | 25 | − |
| 28 | 6.25 | − |
| 29 | 400 | − |
| 29 | 100 | − |
| 29 | 25 | − |
| 29 | 6.25 | − |
| 30 | 400 | − |
| 30 | 100 | − |
| 30 | 25 | − |
| 30 | 6.25 | − |
| 31 | 400 | − |
| 31 | 100 | − |
| 31 | 25 | − |
| 31 | 6.25 | − |
| 32 | 400 | − |
| 32 | 100 | − |
| 32 | 25 | − |
| 32 | 6.25 | − |
| 33 | 400 | + |
| 33 | 100 | + |
| 33 | 25 | − |
| 33 | 6.25 | − |
| 34 | 400 | + |
| 34 | 100 | + |
| 34 | 25 | + |
| 34 | 6.25 | + |
| 35 | 400 | + |
| 35 | 100 | + |
| 35 | 25 | + |
| 35 | 6.25 | + |
| 36 | 400 | + |
| 36 | 100 | + |
| 36 | 25 | + |
| 36 | 6.25 | − |

| COMPOUND NUMBER | RATE (ppm) | PMW |
|---|---|---|
| 37 | 400 | + |
| 37 | 100 | + |
| 37 | 25 | + |
| 37 | 6.25 | − |
| 38 | 400 | + |
| 38 | 100 | + |
| 38 | 25 | − |
| 38 | 6.25 | − |
| 39 | 400 | − |
| 39 | 100 | − |
| 39 | 25 | − |
| 39 | 6.25 | − |
| 40 | 400 | − |
| 40 | 100 | − |
| 40 | 25 | − |
| 40 | 6.25 | − |
| 41 | 400 | − |
| 41 | 100 | − |
| 41 | 25 | − |
| 41 | 6.25 | − |
| 42 | 400 | − |
| 42 | 100 | − |
| 42 | 25 | − |
| 42 | 6.25 | − |
| 43 | 400 | + |
| 43 | 100 | − |
| 43 | 25 | − |
| 43 | 6.25 | − |
| 44 | 400 | − |
| 44 | 100 | − |
| 44 | 25 | − |
| 44 | 6.25 | − |
| 45 | 400 | − |
| 45 | 100 | − |
| 45 | 25 | − |
| 45 | 6.25 | − |
| 46 | 400 | − |
| 46 | 100 | − |
| 46 | 25 | − |
| 46 | 6.25 | − |
| 47 | 400 | − |
| 47 | 100 | − |
| 47 | 25 | − |
| 47 | 6.25 | − |
| 48 | 400 | − |
| 48 | 100 | − |
| 48 | 25 | − |
| 48 | 6.25 | − |
| 49 | 400 | − |
| 49 | 100 | − |
| 49 | 25 | − |
| 49 | 6.25 | − |
| 50 | 400 | + |
| 50 | 100 | + |
| 50 | 25 | − |
| 50 | 6.25 | − |
| 51 | 400 | − |
| 51 | 100 | − |
| 51 | 25 | − |
| 51 | 6.25 | − |
| 52 | 400 | − |
| 52 | 100 | − |
| 52 | 25 | − |
| 52 | 6.25 | − |
| 53 | 400 | + |
| 53 | 100 | + |
| 53 | 25 | + |
| 53 | 6.25 | + |
| 54 | 400 | + |
| 54 | 100 | − |
| 54 | 25 | − |
| 54 | 6.25 | − |
| 55 | 400 | + |
| 55 | 100 | + |
| 55 | 25 | + |
| 55 | 6.25 | + |
| 56 | 400 | + |
| 56 | 100 | + |
| 56 | 25 | + |
| 56 | 6.25 | − |
| 57 | 400 | + |
| 57 | 100 | + |
| 57 | 25 | + |
| 57 | 6.25 | + |
| 58 | 400 | + |
| 58 | 100 | + |
| 58 | 25 | + |
| 58 | 6.25 | + |

NT = not tested against specific organism
0 = 0% control
− = 1–49% control
+ = 50–100% control The compounds of this invention are made using well known chemical procedures. The required starting materials are commercially available, or readily synthesized utilizing standard procedures, several of which are disclosed in U.S. Pat. No. 5,145,843. The compounds of formula (1) are then prepared by treatment of the corresponding 4-V substituted lepidine derivative with the appropriate —Z—A containing derivative.

The following nonlimiting examples further illustrate this invention.

EXAMPLE 1

4-((4-Fluorophenyloxy)methyl)-8-Chloroquinoline

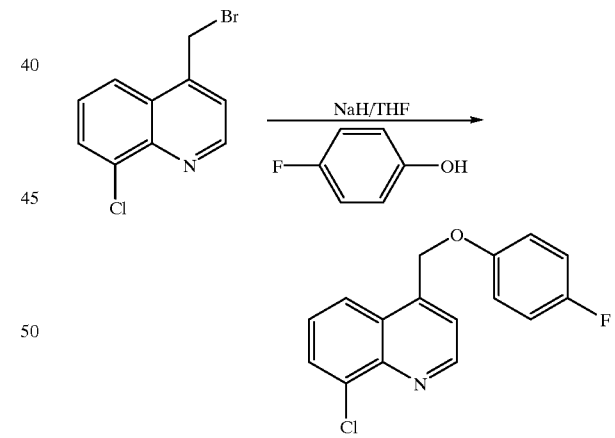

4-Bromomethyl-8-chloroquinoline (0.8 g, 3.11 mmol) was dissolved with stirring in dry THF (10 mls) and sodium hydride (0.15 g, 60% dispersion in mineral oil, 6.23 mmol) added. The mixture was stirred at room temperature for 15 minutes and 4-fluorophenol (0.52 g, 3.11 mmol) added. The mixture was stirred at room temperature overnight and worked up to provide the product (0.46 g, 51.2%) as a white solid, mp 144–5° C.

Found: C, 66.41; H, 3.67; N, 4.88%; calculated: C, 66.87; H, 3.67; N, 4.88%

EXAMPLE 2

4-(2-Phenylethenyl)-7-chloroquinoline

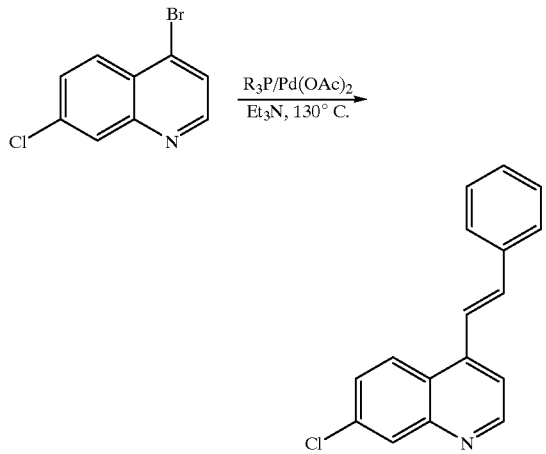

A mixture of 4-bromo-7-chloroquinoline (24.3 g, 0.1 mol), styrene (12.0 g, 0.125 mol), tri(o-tolyl) phosphine (0.4 g, 1.3 mmol), palladium acetate (0.2 g, 0.89 mol) and triethylamine (120 mls) was charged into a 300 ml stirred pressure vessel and heated at 120° C. for 17 hours. The mixture was cooled, filtered to remove triethylamine hydrobromide, and the solids washed with ethyl acetate (250 ml). Solvents were evaporated under reduced pressure and the residue dissolved in ethyl acetate (500 ml). The solution was washed with water and brine, and dried over anhydrous sodium sulphate. Evaporation of the solvent under reduced pressure and recrystallisation of the residue from ethyl acetate: hexane gave the product (13.5 g, 51%) as an orange solid, mp 120–122° C.

Found: C, 76.50; H, 4.62; N, 5.38%; calculated: C, 76.84; H, 4.55; N, 5.27%

EXAMPLE 3

4-((3-Trifluoromethyl-2-pyridinyloxy)methyl)-7-chloroquinoline

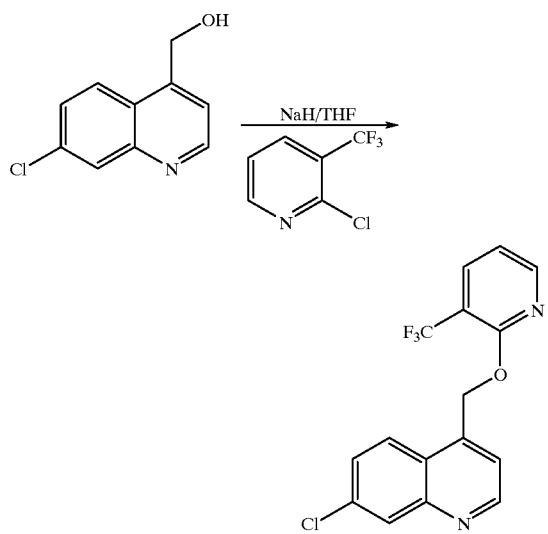

4-Hydroxymethyl-7-chloroquinoline (0.6 g, 3.12 mmol) was dissolved with stirring in dry THF (20 mls) and sodium hydride (0.15 g, 60% dispersion in mineral oil, 3.75 mmol) added. The mixture was stirred at room temperature for one hour and 2-chloro-3-trifluoromethylpyridine (0.62 g, 3.42 mmol) added. The mixture was stirred overnight and worked up to provide the product (0.9 g, % as a tan solid, mp 125–7° C.

Found: C, 56.68; H, 2.90; N, 8.17%; calculated: C, 56.74; H, 2.98; N, 8.27%

EXAMPLE 4

4-[1-[(4-Fluorophenyl)oxy]ethyl]-5,7-dichloroquinoline

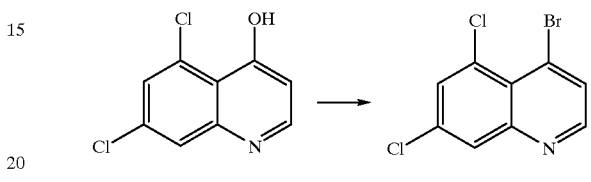

Bromine (15 ml, 0.30 mol) was dissolved in acetonitrile (200 ml) and added dropwise to a suspension of 4-hydroxy-5,7-dichloroquinoline (60 g, 0.28 mol) (Swiss Pat. CH 93-3640 931207) and triphenylphosphite (78 ml, 0.30 mol) in acetonitrile (1 L) over three hours. The reaction was left to stir for 24 hours at which point it was filtered to collect the precipitate. The solid was suspended between water (1 L) and dichloromethane (500 ml) and neutralized with sodium bicarbonate. Extractions were performed periodically as the aqueous layer neared neutral and finally at pH 10 to give a total of 5×500 ml aliquots. The organics were combined, dried (magnesium sulfate), filtered through a plug of silica gel, and concentrated under vacuum to a total volume of 1 L, then heated until solid dissolved and left to crystallize 12 hours. Filtration gave analytically pure product (46 g, 65%) while concentration of the mother liquor gave spectroscopically clean product (14 g, 20%, mp 131° C.).

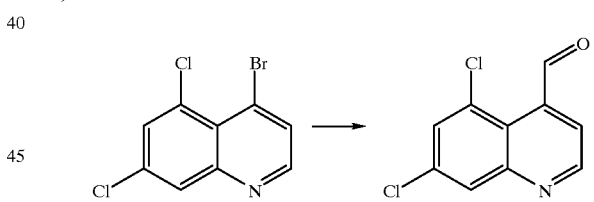

A solution of 4-bromo-5,7-dichloroquinoline (5.7 g, 21 mmol), Palladium(II)acetate (0.93 g, 4.2 mmol), tri-o-tolylphosphine (2.5 g, 8.2 mmol), styrene (5 ml, 26.2 mmol), copper iodide (0.80 g, 4.2 mmol), and triethylamine (4 ml, 28 mmol) in acetonitrile (41 ml) was heated at reflux for three hours. After cooling to ambient temperature, the reaction was diluted with ethyl acetate and filtered through a plug of silica gel. This material was used as is minus an analytical sample (178 mg, mp 242° C.) used for characterization. The resulting solid was taken up in methanol, dichloromethane solution (1:1, 600 ml) and cooled to −78° C. Ozone was passed through the system until the reaction was complete as determined by GCMS. Thiourea was added (5 g, 600 mmol) and left to warm to ambient temperature, filtered through a plug of silica and rinsed with through with dichloromethane. The solvent was removed under vacuum with slight heat until a white solid precipitated. The solid was collected as several crops to give the desired aldehyde (2.1 g, 45% over 2 steps, mp 154° C. ). Analytical samples were obtained by recrystalization from ethylacetate.

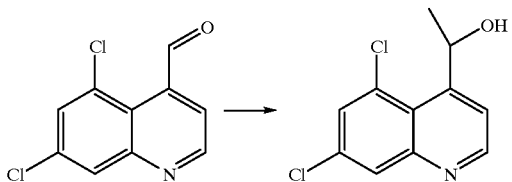

The aldehyde (100 mg, 0.44 mmol) was dissolved in toluene (6 ml) and cooled to 0° C. Methylmagnesium bromide (1.4 M in toluene/tetrahydrofuran) was dripped in until the starting material was exhausted as judged by TLC. The reaction was diluted with ethylacetate (50 ml) and 0.5 N HCl (50 ml) and allowed to warm to ambient temperature. The organic layer was additionally extracted with 0.5 N HCl (3×50 ml). The aqueous layers were combined and neutralized with sodium bicarbonate and extracted with ethylacetate (4×50 ml)the organics were dried (Magnesium sulfate), filtered and concentrated to give clean product (101 mg, 94%, mp 112° C.)

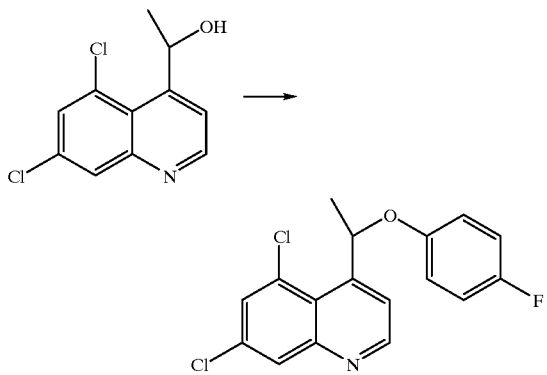

Neat diethyl azodicarboxylate (0.30 ml, 1.9 mmol) was added to a solution of secondary alcohol (300 mg, 1.25 mmol), triphenylphosphine (600 mg, 2.3 mmol), and 4-fluorophenol (200 mg, 1.7 mmol) in chloroform (6 ml) over 15 minutes. The reaction was allowed to stir for two hours, concentrated under vacuum and purified by medium pressure chromatography, (10:1, heptane/ethyl acetate), the resulting solid was recrystalized from pentane to give the phenoxy lepidine (325 mg, 78%, mp 101° C.).

EXAMPLE 5

4-[(4-fluorophenylamino)methyl)]-5,7-dichloroquinoline

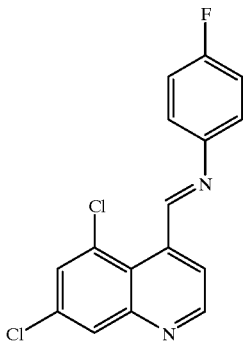

5,7-Dichloroquinoline-4-carboxaldehyde (500 mg, 2.2 mmol) and 4-fluoroaniline (246 mg, 2.2 mmol) were combined in 20 ml benzene with magnetic stirring. The flask was fitted with a Dean-Stark trap and heated to reflux overnight. Reaction was monitored by TLC and shown to be complete after 16 hours. The benzene was removed in vacuo and the resulting solid recrystallized from ethyl acetate/heptane. Yield: 0.5 g (71%), mp 153° C.

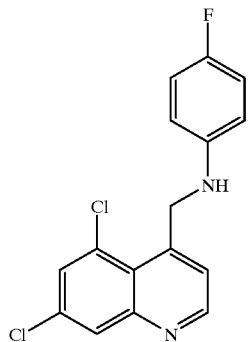

The product above(600 mg, 1.9 mmol) was dissolved in 10 ml ethanol. Sodium borohydride (90 mg, 2.4 mmol) was added and the reaction magnetically stirred overnight at room temperature under nitrogen atmosphere. Reaction was monitored by TLC and shown to be complete. The reaction was diluted with water and extracted with ethyl acetate. The organic layer was dried over magnesium sulfate, filtered and evaporated in vacuo. The resulting solid was recrystallized from ethyl acetate/heptane. Yield: 180 mg (30%), mp 166.5° C.

EXAMPLE 6

4-Hydroxymethyl-5,7-dichlororoquinoline

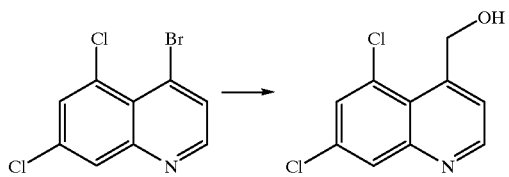

A solution of 4-bromo-5,7-dichloroquinoline (5.7 g, 21 mmol), palladium(II)acetate (0.93 g, 4.2 mmol), tri-o-tolylphosphine (2.5 g, 8.2 mmol), styrene (5 ml, 26.2 mmol), copper iodide (0.80 g, 4.2 mmol), and triethylamine (16 ml, 115 mmol) in acetonitrile (41 ml) was heated at reflux for three hours. After cooling to ambient temperature, the reaction was diluted with ethyl acetate and washed with dilute hydrochloric acid and brine. The organic layer was dried (MgSO$_4$) and concentrated to a white solid. The solid was taken up in a methanol/dichloromethane solution (1:1, 400 ml) and cooled to −78° C. Ozone was passed through the system until the reaction was complete as determined by GCMS. Thiourea was added (5.0 g, 600 mmol) and left to warm to ambient temperature. The reaction was diluted with dichloromethane and filtered through a plug of silica gel eluting with methanol/dichloromethane (1:1). The solution was cooled to 0° C. and sodium borohydride was added as a solid over one hour until the reaction was deemed complete by GCMS. The reaction was quenched and washed with 1N hydrochloric acid. The aqueous layers were combined and filtered through a plug of cotton and then neutralized with sodium bicarbonate. The solid was collected by filtration and air dried to give the desired product (2.8 g, in >80% purity. An analytical sample was prepared via recrystalization from ethyl acetate/methanol (mp 196° C.).

EXAMPLE 7

4-Hydroxymethyl-7-chloroquinoline

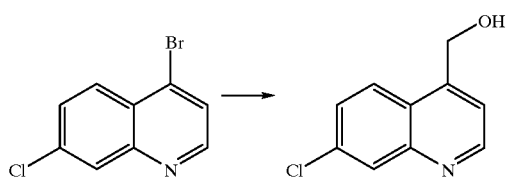

A 200 ml stainless steel autoclave was loaded with 4-bromo-7-chloroquinoline (1.2 g, 5.0 mmol) (Can. Pat. CA 94-2133620 941004), bis(triphenylphosphine)palladium chloride (0.1 g), triethylamine (3 ml) and ethanol (40 ml) and pressurized to 200 psi with carbon monoxide. The autoclave was heated at 120° C. for 12 hours, cooled, and vented. Solids were removed by filtration through celite and the mother liquor concentrated in vacuo. The residue was taken up in chloroform (50 ml), washed with water (3×50 ml), saturated brine (50 ml), and dried ($Na_2SO_4$). Filtration and removal of solvent left 1.3 g of a brown liquid. Flash chromatography on silica using 1 vol % $CH_3CN$ in $CH_2Cl_2$ as eluent afforded product as a colorless syrup which solidified to a waxy solid. This solid was dissolved in methanol (50 ml) and sodium borohydride was added over two hours until judged complete by TLC. The reaction was diluted with water and acidified with 1N hydrochloric acid and then neutralized with sodium bicarbonate. The resulting solid was recovered via filtration, dissolved in ethyl acetate and dried ($MgSO_4$). Filtration and concentration afforded the desired compound (mp: 160° C., 0.66 g, 68% over two steps).

EXAMPLE 8

8-Chlorolepidine

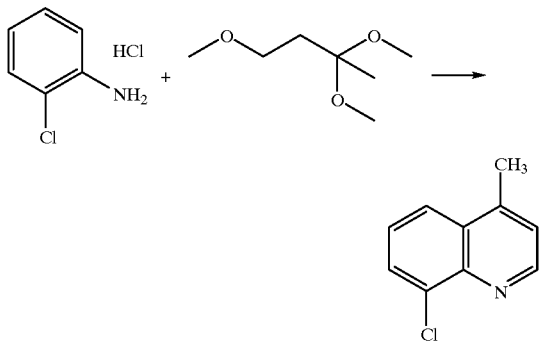

Commercially available 2-chloroaniline (200 g, 1.56 mol) was dissolved in 600 ml ethanol, and dry HCl gas was bubbled through for 10 minutes to give 2-chloroaniline hydrochloride. A new flask was charged with 2-chloroaniline hydrochloride (130 g, 0.793 mol), ferric chloride hexahydrate (25.7 g, 0.095 mol), anhydrous zinc chloride (10.9 g, 0.0799 mol) and 500 ml 2B ethanol. The mixture was heated to 60° C. for 10 minutes and 1,3,3-trimethoxy butane was added dropwise over a period of one hour. The mixture was then refluxed for two hours and allowed to stand overnight at room temperature. Most of the alcohol was removed by distillation and the residue was made alkaline with 25% sodium hydroxide solution. The reaction was cooled, filtered, and the filter pad washed with toluene. The toluene was concentrated to dryness. The product was recrystallized from dichloromethane/pentane to obtained a spectroscopically pure sample (mp: 110° C., 37.0 g, 25% overall yield).

EXAMPLE 9

4-Bromomethyl-8-chloroquinoline

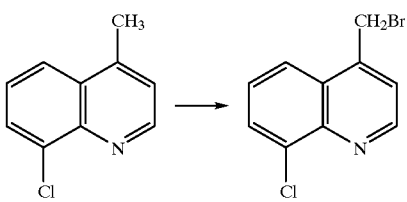

The 8-chlorolepidine (20.0 g, 0.113 mol) and N-bromosuccinimide, (20.0 g, 0.113 mol) were dissolved in 200 ml dry carbon tetrachloride and the mixture stirred under nitrogen for three hours, while being exposed to a 250 watt high intensity sun lamp. The solution was cooled to room temperature, filtered, and evaporated to dryness. The residue was placed over a silica gel column using ethyl acetate/pentane, to give the bromomethyl lepidine (10.8 g, 37.4% yield, mp: 92° C.)

EXAMPLE 10

7-Chloro-α-(trifluoromethyl)-4-quinolinemethanol

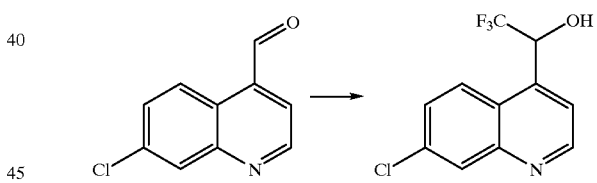

4-Carboxaldehyde-7-chloro quinoline (1.00 g, 5.22 mmol) was dissolved in 12.5 ml of a 0.5 M solution of trimethyl(trifluoromethyl)silane in tetrahydrofuran in an oven dried, nitrogen swept 100 ml round bottomed flask, and the resulting solution was cooled to 0° C. under nitrogen. With stirring, tetra-n-butyl ammonium fluoride trihydrate (0.014 g, 0.052 mmol) was added as a solid and the mixture allowed to warm slowly to room temperature over two hours by which time thin layer chromatography (hexanes:ethyl acetate/2:1) indicated complete consumption of the starting material. The reaction mixture was cooled to 0° C. and 10% aqueous hydrochloric acid (3 ml) was added and the mixture stirred at room temperature until cleavage of the trimethyl silyl ether was complete as indicated by thin layer chromatography (1 h). The reaction mixture was partitioned between saturated sodium hydrogen carbonate and ethyl acetate, the layers separated and the aqueous layer extracted with an additional portion of ethyl acetate. The combined organic layers were dried ($MgSO_4$) filtered and concentrated to dryness. Purification by flash silica gel chromatography (hexanes:ethyl acetate/2:1) provided 7-chloro-α-(trifluoromethyl)-4-quinolinemethanol (1.32 g, 96%) as a yellow solid. An analytical sample was prepared by recrystallization from ethyl acetate:hexanes. (mp 161° C.).

EXAMPLE 11

5-Fluoro-2-(methylsulfonyl)-pyrimidine

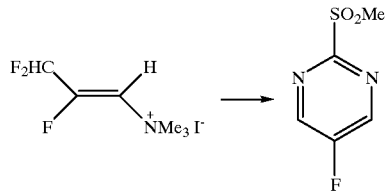

N-(2,3,3-Trifluoro-1-propenyl)trimethylammonium iodide (10.0 g, 35.6 mmol) (*Tetrahedron Lett.* 1995, 36(9), 1527) was dissolved in 70 ml of acetonitrile in a oven dried nitrogen swept 250 ml round bottomed flask. With stirring, diethylamine (15.6 g, 213 mmol) was added via syringe, the flask was fitted with a reflux condenser and stirred under nitrogen at 75–80° C. for one hour. The mixture was allowed to cool to room temperature and 2-methyl-2-thiopseudourea sulfate (19.8 g, 71.2 mmol) and sodium methoxide (3.80 g, 71.2 mmol, 15 ml of a 25% solution in methyl alcohol) were added with stirring and the mixture heated to reflux for six hours. The cooled reaction mixture was poured into water, the layers separated, the aqueous phase extracted with methylene chloride (3×50 ml) and the combined organics were dried (sodium sulfate), filtered and concentrated to low volume. Purification by flash silica gel chromatography (hexanes:ethyl acetate/10:1) provided the volatile 5-fluoro-2-(thiomethyl) pyrimidine, which was immediately dissolved in 100 ml of methylene chloride in a 500 ml round bottomed flask, and treated at 0° C. with 3-chloroperoxybenzoic acid (21.6 g, 125 mmol) with good stirring. After stirring for 15 hours at room temperature, the oxidation was judged complete by thin layer chromatography (hexanes:ethyl acetate/1:2). The reaction mixture was poured into saturated sodium hydrogen carbonate, the layers separated and the aqueous phase extracted with methylene chloride and the combined organics washed with saturated sodium hydrogen carbonate and dried (NaSO$_4$), filtered and concentrated. Purification by flash silica gel chromatography (hexanes:ethyl acetate/1:2) provided 5-fluoro-2-(methylsulfonyl) pyrimidine (4.3 g, 68% (from N-(2,3,3-trifluoro-1-propenyl) trimethylammonium iodide) as colorless oil: p Analysis calcd for $C_5H_5F_1N_2O_2S$: C, 34.09; H, 2.86; N, 15.9; S, 18.2. Found: C, 34.09; H, 2.79; N, 15.81; S, 18.3.

EXAMPLE 12

7-Chloro-4-[2,2,2-trifluoro-1-[(5-fluoro-2-pyrimidinyl)oxy]ethyl]quinoline

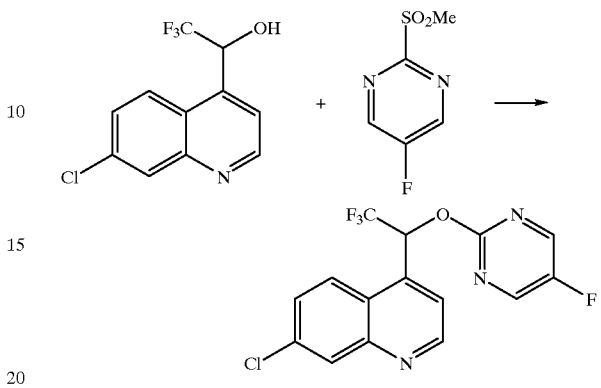

7-Chloro-α-(trifluoromethyl)-4-quinolinemethanol (0.25 g, 0.96 mmol) was dissolved in 5 ml of tetrahydrofuran in a oven dried, nitrogen swept 25 ml round bottomed flask and the resulting solution was cooled to 0° C. under nitrogen. With stirring, NaH (0.042 g, 1.1 mmol, 60% dispersion in mineral oil) was added all at once. After 15 minutes, 5-fluoro-2-(methylsulfonyl) pyrimidine (0.17 g, 0.96 mmol) was added dropwise via syringe as a solution in tetrahydrofuran (2.5 ml) over 5 minutes. An additional 2 ml of tetrahydrofuran was used to rinse the flask containing the sulfone and the syringe. The milky solution was allowed to warm to room temperature and stir for 15 hours by which time thin layer chromatography (hexanes:ethyl acetate/1:1) indicated complete consumption of the starting materials. The reaction mixture was partitioned between water and ethyl acetate, the layers separated and the aqueous layer extracted with an additional portion of ethyl acetate. The combined organic layers were dried (MgSO$_4$) filtered and concentrated to dryness. Purification by flash silica gel chromatography (hexanes:ethyl acetate/2:1) provided 7-chloro-4-[2,2,2-trifluoro-1-[(5-fluoro-2-pyrimidinyl) oxy] ethyl]quinoline (0.32 g, 94%) as a white solid. An analytical sample was prepared by recrystallization from hexane. (mp 92° C.).

The following table identifies compounds of formula (1) prepared analogous to the various processes illustrated in the preceding examples.

| Cmpd No. | R$^1$–R$^4$ | X | Y | V | Z | A | m.p (° C.) |
|---|---|---|---|---|---|---|---|
| 1 | 7-Cl | CH | CH | CHCH$_3$ | O | 4-fluorophenyl | 104–106 |
| 2 | 7-Cl | CH | CH | CHC$_6$H$_{13}$ | O | 4-fluorophenyl | 38–40 |
| 3 | 7-Cl | CH | CH | CHCN | O | 4-fluorophenyl | 118–123 |
| 4 | 7-Cl | CH | CH | CHCH=CH$_2$ | O | 4-fluorophenyl | 186–190 |
| 5 | 7-Cl | CH | CH | CH$_2$ | O | 2,5-trifluoromethyl-6-pyridinyl | 83–85 |
| 6 | 7-Cl | CH | CH | CH$_2$ | O | 4,6-methoxy-2-pyrimidinyl | 134–136 |
| 7 | 5,7-diCl | CH | CH | CH$_2$ | O | 2-trifluoromethyl-6-pyridinyl | 108.1–110.1 |
| 8 | 5,7- | CH | CH | CH$_2$ | O | 4-methoxy-6- | 166–167 |

-continued

| Cmpd No. | R¹–R⁴ | X | Y | V | Z | A | m.p (° C.) |
|---|---|---|---|---|---|---|---|
| | diCl | | | | | methyl-2-pyrimidinyl | |
| 9 | 7-Cl | CH | CH | CH₂ | O | 4-methoxy-6-methyl-2-pyrimidinyl | 114–116 |
| 10 | 5,7-diCl | CH | CH | CH₂ | NCH₃ | 4-fluorophenyl | 118–122 |
| 11 | 5,7-diCl | CH | CH | CH₂ | O | 2-trifluoromethyl-6-pyridinyl | 176.1–178.1 |
| 12 | 5,7-diCl | CH | CH | CH₂ | O | 4-methoxy-2-pyrimidinyl | 211.1–213.1 |
| 13 | 5,7-diCl | CH | CH | CHCH₂CH₃ | O | 4-fluorophenyl | 102–103 |
| 14 | 5,7-diCl | CH | CH | CH₂ | O | 4,6-dimethyl-1,3-pyrimidinyl | 169.4–170.4 |
| 15 | 7-Cl | CH | CH | CH₂ | O | 4-trifluoromethyl-2-pyridinyl | 99–101 |
| 16 | 7-Cl | CH | CH | CH₂ | O | 4,6-dimethyl-1,3-pyrimidinyl | 145–147 |
| 17 | 7-Cl | CH | CH | CH₂ | O | 4-methoxy-2-pyrimidinyl | 125–127 |
| 18 | 7-Cl | CH | CH | CH₂ | O | 6-methyl-2-(trifluoromethyl)pyridinyl | 61–63 |
| 19 | 7-Cl | CH | CH | CH₂ | O | 6-methyl-3-(trifluoromethyl)pyridinyl | 110–112 |
| 20 | 5,7-diCl | CH | CH | CH₂ | O | 6-methyl-4-(trifluoromethyl)pyridinyl | 134.5–136.5 |
| 21 | 7-Cl | CH | CH | CH₂ | O | 2-chloro-4-fluorophenyl | 116.3–117.3 |
| 22 | 7-Cl | CH | CH | CH₂ | O | 2-trifluoromethyl-phenyl | 112–115 |
| 23 | 7-Cl | CH | CH | CH₂ | O | 2-methyl-3-(trifluoromethyl)pyridinyl | 125–127 |
| 24 | 7-Cl | CH | CH | CH₂ | O | 5-chloro-3-fluoro-2-methylpyridinyl | 152–153 |
| 25 | 8-F | CH | CH | CH₂ | O | 2-chlorophenyl | 122–123 |
| 26 | 8-F | CH | CH | CH₂ | O | 4-fluorophenyl | 124–125 |
| 27 | 7-Cl | CH | CH | CH₂ | O | 2,4-fluorophenyl | 83.5–85.5 |
| 28 | 7-Cl | CH | CH | CH₂ | O | 4-(CCH₃)phenyl | 104.5–106 |
| 29 | 7-Cl | CH | CH | CH₂ | O | 2-chlorophenyl | 143–144 |

-continued

| Cmpd No. | R¹–R⁴ | X | Y | V | Z | A | m.p (° C.) |
|---|---|---|---|---|---|---|---|
| 30 | H | CH | CH | CH₂ | O | 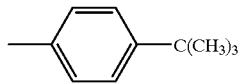 4-t-butylphenyl | 93.5–94.5 |
| 31 | H | CH | CH | CH₂ | O | 2-trifluoromethyl-phenyl | 107.5–108.5 |
| 32 | H | CH | CH | CH₂ | O | 2-chlorophenyl | 92.5–94.5 |
| 33 | 8-F | CH | CH | CH₂ | O | 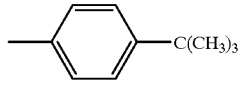 4-t-butylphenyl | 78–81 |
| 34 | 8-Cl | CH | CH | CH₂ | O | 2-chlorophenyl | 122–123 |
| 35 | 5,7-diCl | CH | CH | CHCH₃ | O | 4-fluorophenyl | 104.5–105.5 |
| 36 | 7-Cl | CH | CH | CH₂ | O | 4-fluorophenyl | 133–135 |
| 37 | 5,7-diCl | CH | CH | CH₂ | O | 2-chloro-4-fluoro-phenyl | 142–143 |
| 38 | 8-F | CH | CH | CH₂ | O | phenyl | 101–103 |
| 39 | 8-F | CH | CH | CH₂ | O | 2-trifluoromethyl-phenyl | 128–131 |
| 40 | 8-F | CH | CH | CH₂ | O | 2,4-fluorophenyl | 98–100 |
| 41 | 8-F | CH | CH | CH₂ | O | 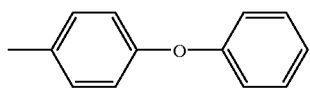 4-phenoxyphenyl | 96–98 |
| 42 | 8-F | CH | CH | CH₂ | O | 2-chloro-4-fluoro-phenyl | 117.5–121.5 |
| 43 | 5,7-diCl | CH | CH | CH₂ | O | 4-phenoxyphenyl | 153–155 |
| 44 | 5,7-diCl | CH | CH | CH₂ | O | 4-t-butylphenyl | 136–137 |
| 45 | 8-Cl | CH | CH | CH₂ | O | 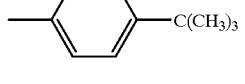 4-t-butylphenyl | 107–109 |
| 46 | 8-Cl | CH | CH | CH₂ | O | 2,4-difluorophenyl | 156–158 |
| 47 | 8-Cl | CH | CH | CH₂ | O | phenyl | 100–102 |
| 48 | 8-Cl | CH | CH | CH₂ | O | 2-trifluorophenyl | 146–148 |
| 49 | 8-Cl | CH | CH | CH₂ | O | 4-fluorophenyl | 144–145 |
| 50 | H | CH | CH | CH₂ | O | 2-chloro-4-fluoro-phenyl | 125.5–126.5 |
| 51 | 8-Cl | CH | CH | CH₂ | O | 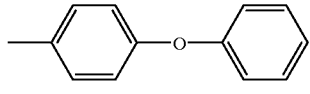 4-phenoxyphenyl | 120–122 |
| 52 | 8-Cl | CH | CH | CH₂ | O | 2-chloro-4-fluoro-phenyl | 132–135 |
| 53 | 5,7-diCl | CH | CH | 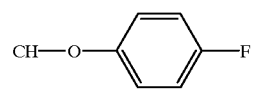 CH—O—(4-fluorophenyl) | O | 4-fluorophenyl | 110–112 |
| 54 | H | CH | CH | CH₂ | O | 4-fluorophenyl | 111–113 |
| 55 | 5,7-diCl | CH | CH | CH₂ | N | 4-fluorophenyl | 167 |
| 56 | 5,7-diCl | CH | CH | CH₂ | O | 2-trifluoromethyl-phenyl | 145–146 |
| 57 | 5,7-diCl | CH | CH | CH₂ | O | 2,4-difluorophenyl | 154–156 |
| 58 | 5,7-diCl | CH | CH | CH₂ | O | 4-fluorophenyl | 133–134 |

The compounds of this invention are applied in the form of compositions, which are important embodiments of the invention, and which comprise one or more compounds of formula (1) with a phytologically-acceptable inert carrier. The composition may optionally include fungicidal combinations which comprise at least 1% of one or more compounds of formula (1) with another fungicide.

The compositions are either concentrated formulations which are dispersed in water for application, or are dust or granular formulations which are applied without further treatment. The compositions are prepared according to procedures which are conventional in the agricultural chemical art, but which are novel and important because of the presence therein of the compounds of this invention. Some description of the formulation of the compositions will, however, be given to assure that agricultural chemists can readily prepare any desired composition.

The dispersions in which the compounds are applied are most often aqueous suspensions or emulsions prepared from concentrated formulations of the compounds. Such water-soluble, water suspendable, or emulsifiable formulations are either solids usually known as wettable powders, or liquids usually known as emulsifiable concentrates or aqueous suspensions. Wettable powders, which may be compacted to form water dispersible granules, comprise an intimate mixture of the active compound, an inert carrier and surfactants. The concentration of the active compound is usually from about 10% to 90%. The inert carrier is usually chosen from among the attapulgite clays, the montmorillonite clays, the diatomaceous earths, or the purified silicates. Effective surfactants, comprising from about 0.5% to about 10% of the wettable powder, are found among the sulfonated lignins, the naphthalenesulfonates, alkylbenzenesulfonates, the alkyl sulfates, and non-ionic surfactants, such as, for example, ethylene oxide adducts of alkyl phenols.

Emulsifiable concentrates of the compounds comprise a convenient concentration of a compound, such as from about 10% to about 50% of liquid, dissolved in an inert carrier, which is either a water miscible solvent or a mixture of water-immiscible organic solvents, and emulsifiers. Useful organic solvents include aromatics, especially the high-boiling naphthalenic and olefinic portions of petroleum such as heavy aromatic naphtha. Other organic solvents may also be used, such as, for example, terpenic solvents, including rosin derivatives, aliphatic ketones, such as cyclohexanone, and complex alcohols, such as 2-ethoxyethanol. Suitable emulsifiers for emulsifiable concentrates are chosen from conventional nonionic surfactants, such as those mentioned above.

Aqueous suspensions comprise suspensions of water-insoluble compounds of this invention, dispersed in an aqueous vehicle at a concentration in the range from about 5% to about 50%. Suspensions are prepared by finely grinding the compound, and vigorously mixing it into a vehicle comprised of water and surfactants chosen from the same types discussed above. Inert ingredients, such as inorganic salts and synthetic or natural gums, may also be added, to increase the density and viscosity of the aqueous vehicle. It is often most effective to grind and mix the compound at the same time by preparing the aqueous mixture, and homogenizing it in an implement such as a sand mill, ball mill, or piston-type homogenizer.

The compounds may also be applied as granular compositions, which are particularly useful for applications to the soil. Granular compositions usually contain from about 0.5% to about 10% of the compound, dispersed in an inert carrier which consists entirely of in large part of clay or a similar inexpensive substance. Such compositions are usually prepared by dissolving the compound in a suitable solvent, and applying it to a granular carrier which has been pre-formed to the appropriate particle size, in the range of from about 0.5 to 3 mm. Such compositions may also be formulated by making a dough or past of the carrier and compound, and crushing and drying to obtain the desired granular particle.

Dusts containing the compounds are prepared simply by intimately mixing the compound in powdered form with a suitable dusty agricultural carrier, such as, for example, kaolin clay, ground volcanic rock, and the like. Dusts can suitably contain from about 1% to about 10% of the compound.

What is claimed is:

1. A compound of formula (1)

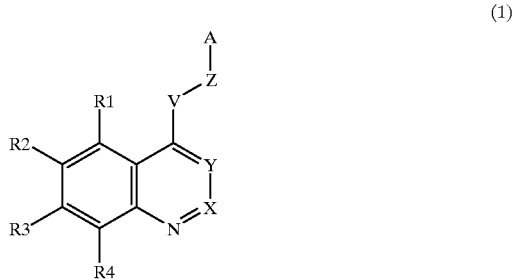

wherein

X is $CR^5$, where $R^5$ is H, Cl or $CH_3$;

Y is $CR^{5'}$ where $R^{5'}$ is H, Cl, or Br;

Z is O;

$R^1$–$R^4$ are independently H, OH, $NO_2$, halo, I, $C_1$–$C_4$ alkyl, $C_3$–$C_4$ branched alkyl, $C_1$–$C_4$ alkoxy, halo $C_1$–$C_4$ alkyl, halo $C_1$–$C_4$ alkoxy, or halo $C_1$–$C_4$ alkylthiol;

V is $CR^7R^8$ where $R^7$ and $R^8$ are independently H, $C_1$–$C_4$ alkyl, $C_1$–$C_4$ alkenyl, $C_2$–$C_4$ alkynyl, $C_1$–$C_4$ acyl, CN, optionally substituted phenoxy, halo $C_1$–$C_4$ alkyl, or OH;

A is a phenyl group of formula (2)

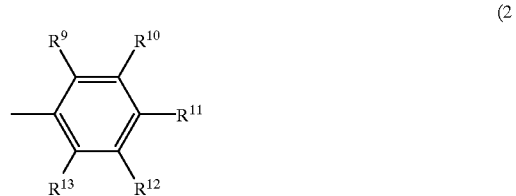

wherein $R^9$–$R^{13}$ are independently H, CN, $NO_2$, OH, halo, $C_1$–$C_4$ alkyl, $C_3$–$C_4$ branched alkyl, $C_2$–$C_4$ alkanoyl, halo $C_1$–$C_7$ alkyl, hydroxy $C_1$–$C_7$ alkyl, $C_1$–$C_7$ alkoxy, halo $C_1$–$C_7$ alkoxy, $C_1$–$C_7$ alkylthio, halo $C_1$–$C_7$ alkylthio, phenyl, substituted phenyl, phenoxy, substituted phenoxy, phenylthio, substituted phenylthio, phenyl $C_1$–$C_4$ alkyl, substituted phenyl $C_1$–$C_4$ alkyl, benzoyl, $SiR^{20}R^{21}R^{22}$ or $OSiR^{20}R^{21}R^{22}$, where $R^{20}$, $R^{21}$, and $R^{22}$ are H, a $C_1$–$C_6$ straight chain or branched alkyl group, phenyl, or substituted phenyl, provided that at least one of $R^{20}$, $R^{21}$, and $R^{22}$ is other than H, or $R^{11}$ and $R^{12}$ or $R^{12}$ and $R^{13}$ combine to form a carbocyclic ring, provided that unless all of $R^9$–$R^{13}$ are H or F, then at least two of $R^9$–$R^{13}$ are H;

or an N-oxide of a compound of formula (1) where Y is CH.

2. A compound of claim 1 wherein

X is CH;

Y is CH;

Z is O;

$R^1$–$R^4$ are independently H, halo, or $C_1$–$C_4$ alkyl;

V is CH or $C_2$–$C_4$ alkyl; and $R^9$–$R^{13}$ are independently halo, $C_1$–$C_4$ alkyl, or halo $C^1$–$C^7$ alkyl.

3. A compound of claim 2 wherein $R^1$–$R^4$ are halo;

A is a phenyl group of formula (2), above, wherein $R^9 R^{13}$ are independently halo.

4. The compound 4-[1-[4-fluorophenyl)oxy]ethyl]-7-chloroquinoline.

5. The compound 4-(cyano(4-fluorophenoxy)methyl)-7-chloroquinoline.

6. The compound 4-[1-[(4-fluorophenyl)oxy]but-4-enyl]-7-chloroquinoline.

7. The compound 4-[6-trifluoromethyl-2-pyridinyloxymethyl]-7-chloroquinoline.

8. The compound 4-[(4-trifluoromethyl-2-pyridinyloxymethyl-5,7-dichloroquinoline.

9. The compound 4-[1-[(4-fluorophenyl)oxy]ethyl]-5,7-dichloroquinoline.

10. The compound 4-[di-(4-fluorophenoxy)]methyl]-5,7-dichloroquinoline.

11. The compound 4-[(4-fluorophenoxy)methyl]-quinoline.

12. The compound 4-[(2,4-difluorophenoxy)methyl]-5,7-dichloroquinoline.

13. The compound 4-[(4-fluorophenoxy)methyl]-5,7-dichloroquinoline.

* * * * *